United States Patent
Scherling et al.

(10) Patent No.: US 6,919,360 B2
(45) Date of Patent: Jul. 19, 2005

(54) BENZISOTHIAZOLYL-SUBSTITUTED AMINOMETHYL CHROMANES FOR TREATING DISEASES OF THE CENTRAL NERVOUS SYSTEM

(75) Inventors: Dietrich Scherling, Freiburg (DE); Wolfgang Karl, Odenthal (DE); Dietrich Seidel, Wuppertal (DE); Corinna Weinz, Wuppertal (DE); Rudolf Schohe-Loop, Wuppertal (DE); Frank Mauler, Overath (DE)

(73) Assignee: Bayer HealthCare AG, Leverkusen (DE)

( * ) Notice: Subject to any disclaimer, the term of this patent is extended or adjusted under 35 U.S.C. 154(b) by 0 days.

(21) Appl. No.: 10/490,315

(22) PCT Filed: Sep. 18, 2002

(86) PCT No.: PCT/EP02/10447

§ 371 (c)(1),
(2), (4) Date: Aug. 18, 2004

(87) PCT Pub. No.: WO03/029250

PCT Pub. Date: Apr. 10, 2003

(65) Prior Publication Data

US 2004/0259924 A1 Dec. 23, 2004

(30) Foreign Application Priority Data

Oct. 1, 2001 (DE) .......................... 101 48 425

(51) Int. Cl.$^7$ .................... A61K 31/428; C07D 417/12
(52) U.S. Cl. .................. 514/367; 548/159; 514/456
(58) Field of Search ................ 548/159; 514/367; 549/373

(56) References Cited

U.S. PATENT DOCUMENTS

| 5,137,901 A | 8/1992 | Junge et al. ............. 514/373 |
| 5,942,529 A | 8/1999 | Schohe-Loop et al. ..... 514/373 |

FOREIGN PATENT DOCUMENTS

| DE | 19543476 | 11/1995 | |
| DE | 19543476 A1 * | 5/1997 | ......... A61K/31/425 |

* cited by examiner

Primary Examiner—Joseph K. McKane
Assistant Examiner—Janet L Coppins
(74) Attorney, Agent, or Firm—Susan M. Pellegrino

(57) ABSTRACT

The present invention relates to chromans, to processes for their preparation and to their use in medicaments, in particular as agents for treating disorders of the central nervous system.

5 Claims, No Drawings

BENZISOTHIAZOLYL-SUBSTITUTED AMINOMETHYL CHROMANES FOR TREATING DISEASES OF THE CENTRAL NERVOUS SYSTEM

The present invention relates to chromans, to processes for their preparation and to their use in medicaments, in particular as agents for treating disorders of the central nervous system.

Chromans having affinity to or agonistic action at the serotonin receptor of subtype $5HT_1$ or $5HT_{1A}$ in particular for treating disorders of the central nervous system are known from DE-A-195 43 476, EP-A-0 352 613, EP-A-0 749 970 and WO 99/26621.

BAY x3702, (−)-2-(4-{[(2R)-3,4-dihydro-2H-chromen-2-ylmethyl]amino}butyl)-1,2-benzisothiazol-3(2H)-one 1,1-dioxide hydrochloride (non-proprietary name: repinotan hydrochloride) is undergoing clinical development for the indications skull-brain trauma and stroke (De Vry et al. Drugs Fut. 1997, 22, 341–349).

Surprisingly, it has been found that metabolites of repinotan also bind to the $5HT_{1A}$ receptor.

Accordingly, the invention relates to novel compounds of the general formula (I),

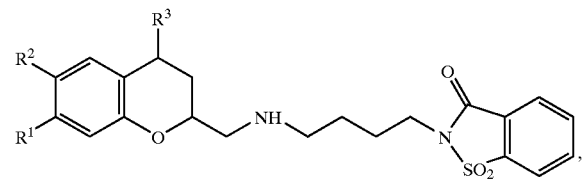

(I)

in which
the radicals $R^1$, $R^2$ and $R^3$ are as defined below:

| $R^1$ | $R^2$ | $R^3$ |
|---|---|---|
| OH | H | H; |
| H | OH | H; |
| H | H | OH; |
| OH | OH | H; |
| OH | H | OH; |
| H | OH | OH or |
| OH | OH | OH, |

The compounds according to the invention may exist in stereoisomeric forms which are related either as image and mirror image (enantiomer), or which are not related as image and mirror image (diasteromers). The invention relates both to the enantiomers or diasteromers and to their respective mixtures. These mixtures of enantiomers and diasteromers can be separated in a known manner to the stereoisomerically pure constituents.

The compounds according to the invention can also be present in the form of their salts, hydrates and/or solvates.

In the context of the invention, preferred salts are physiologically acceptable salts of the compounds according to the invention.

Physiologically acceptable salts of the compounds according to the invention can be acid addition salts of the compounds with mineral acids, carboxylic acids or sulfonic acids. Particular preference is given, for example, to salts with hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, citric acid, fumaric acid, maleic acid or benzoic acid.

Hydrates of the compounds according to the invention are stoichiometric compositions of the compounds or its salts with water.

Solvates of the compounds according to the invention are stoichiometric compositions of the compounds or its salts with solvent.

if appropriate in an isomeric form, and salts thereof.

Preference is given to compounds of the general formula (I) having the R configuration in the 2-position of the chroman radical.

The R configuration in the 2-position of the chroman radical can be illustrated by the formula below:

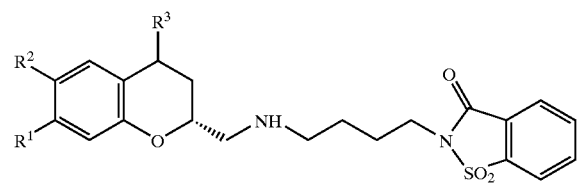

The compounds of the general formula (I) according to the invention can be prepared as illustrated in the formula schemes below and as described in the working examples:

Scheme 1

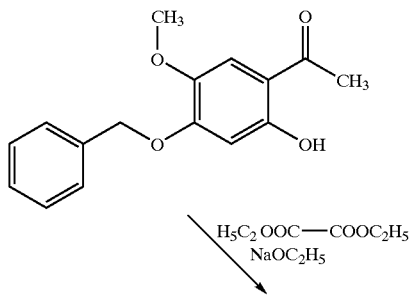

-continued
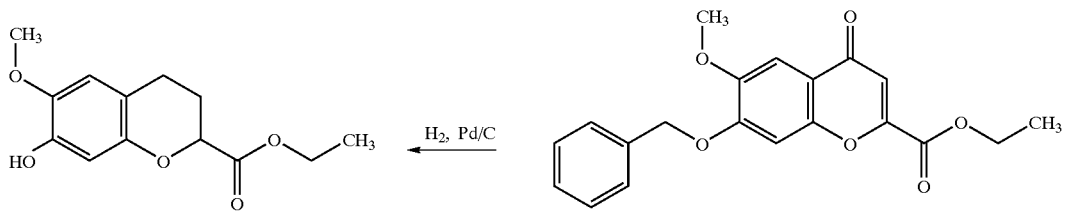
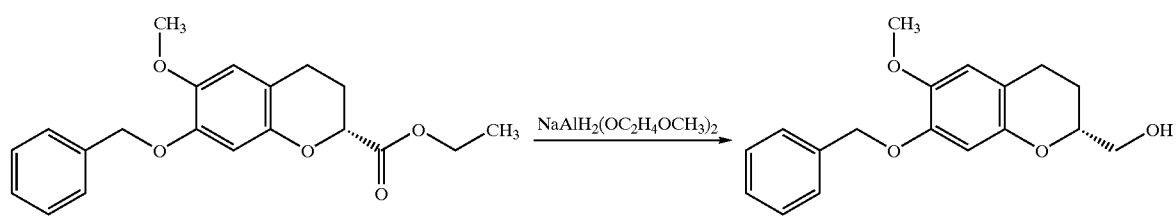
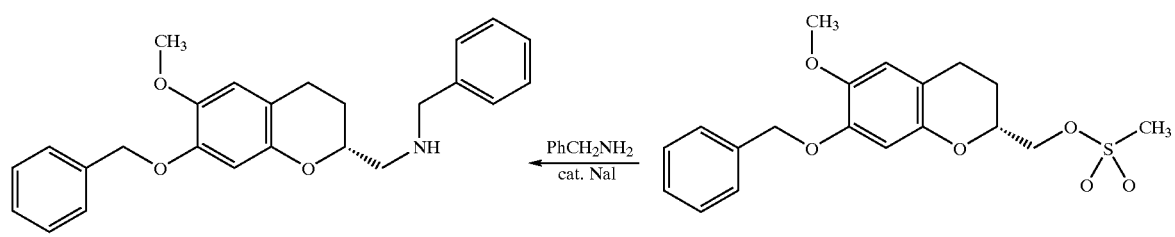
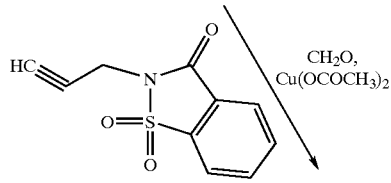
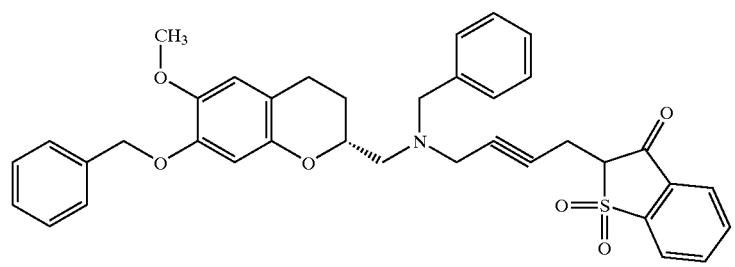

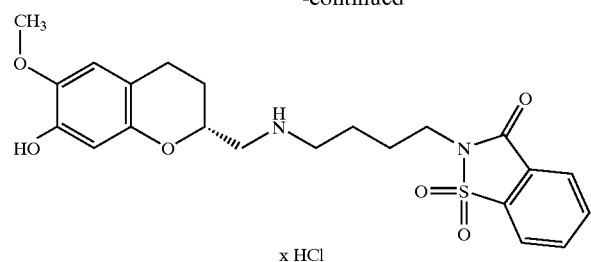
Scheme 2
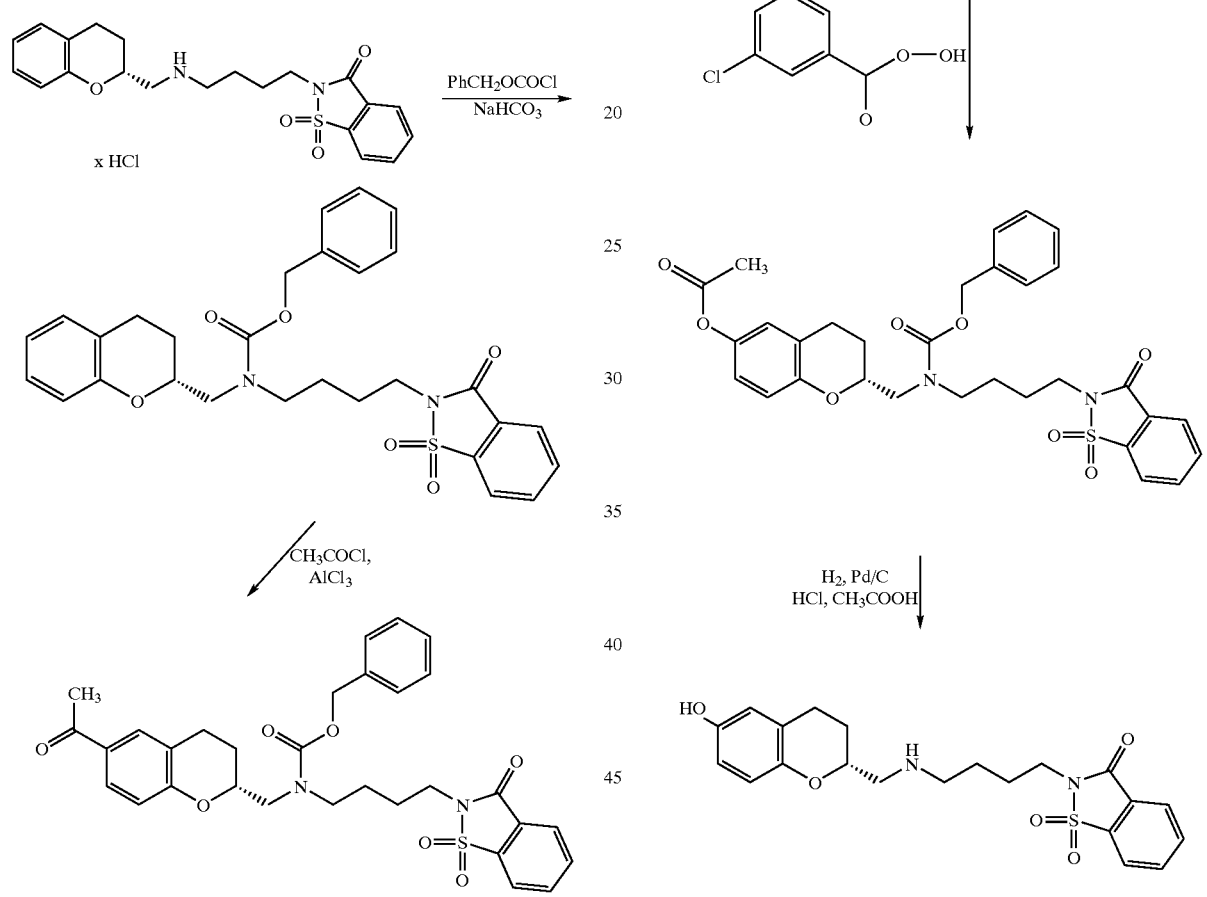
Scheme 3
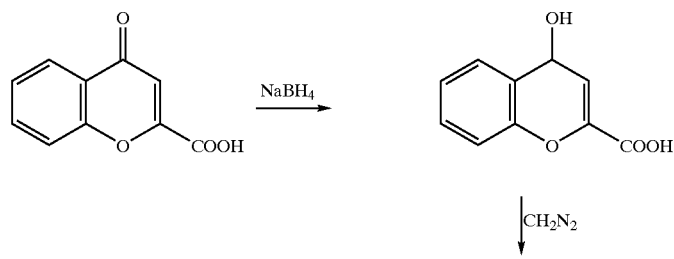

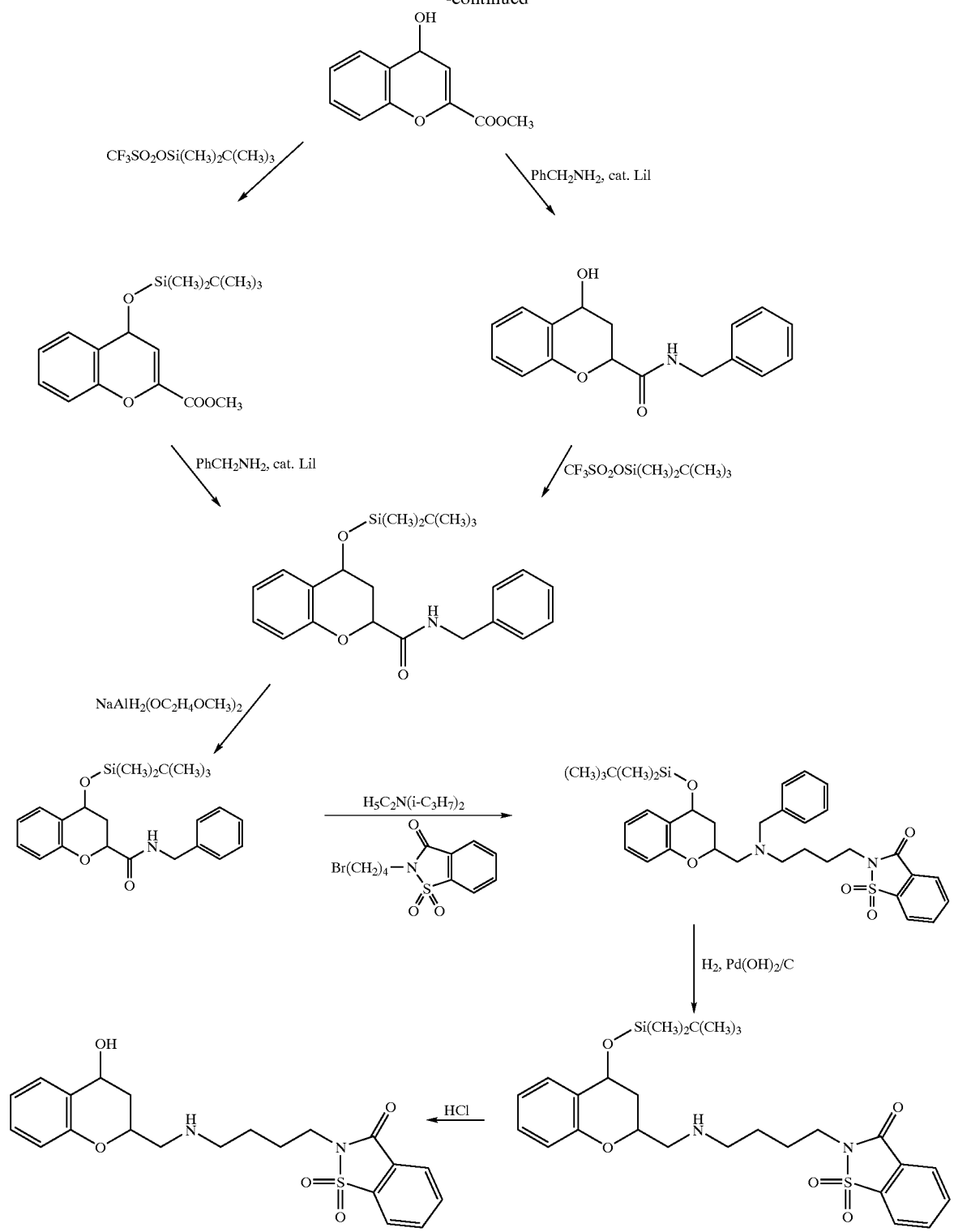

The compounds according to the invention can be used as active compounds in medicaments. The compounds according to the invention have particularly high affinity to cerebral 5-hydroxytryptamine receptors of the $5\text{-HT}_{1A}$ type.

The compounds described in the present invention are thus active compounds for treating diseases which are characterized by disorders of the serotoninergic system, in particular in involvement of receptors of the $5\text{-HT}_{1A}$ type. They are therefore suitable for the treatment of disorders of the central nervous system such as states of anxiety, tension and depression, central nervous system-related sexual dysfunctions and sleep disorders, and for the regulation of pathological disorders related to the intake of food, stimulants and addictive substances. They are furthermore suitable for removing cognitive deficits, for improving learning and memory performances and for treating Alzheimer's disease.

These active compounds are furthermore also suitable for modulating the cardiovascular system. They also intervene in the regulation of cerebral perfusion and are thus effective agents for controlling migraine.

Moreover, the compounds of the general formula (I) and the pharmaceutical compositions derived from these compounds can, as has been shown in WO 99/26621 for other $5HT_{1A}$ ligands, be used for post-acute therapeutic treatment of multifarious neurological disorders where different cell types of the nervous system are degenerated and/or have been damaged as a result of neurodegenerative disorders or interventions or exposures. Compounds of the general formula (I) can be used in particular for treating sequelae in which cells of the nervous system have been damaged by surgical interventions, infections, exposure to toxic agents, tumors, malnutrition or metabolic disorders. Moreover, compounds of the general formula (I) can be used for treating the effects of neurodegenerative disorders such as Parkinson's disease, multiple sclerosis, amyotrophic lateral sclerosis, epilepsy, drug abuse or drug addiction (alcohol, cocaine, heroin, amphetamine or the like), myelopathies and/or spinal injuries, dystrophy or degeneration of the neutroretina (retinopathies) and peripheral neuropathies, such as diabetic neuropathy and/or peripheral neuropathies induced by toxins. Moreover, compounds of the general formula (I) can be used in connection with surgical implantations of tissue and/or prostheses for treating Alzheimer's disease or other neurological disorders and/or dysfunctions where an implantation is indicated.

The in vitro action of the compounds according to the invention can be demonstrated in the following assays:
1. Affinity to the $5\text{-}HT_{1A}$ Receptor
(Dompert et al., *Naunyn-Schmiedeberg's Arch. Pharmacol.* 1985, 328, 467–470).

In this test, binding of [$^3$H]-8-OH-DPAT to $5\text{-}HT_{1A}$ receptors in hippocampus membranes of rats is measured. It was found that the compounds according to the invention compete with the radio ligand for the binding site, inhibiting it.

TABLE B

| Compound of Example | $K_i$ (nmol/l) |
|---|---|
| 1 | 3.15 |
| 2 | 1.93 |

In the binding test, $IC_{50}$ values are determined which state at which concentration of test substance 50% of bound radio ligand is displaced. Taking into account the dissociation constants and the concentration of radio ligand, this is used to calculate the inhibition constant $K_i$.

That the compounds according to the invention are suitable for treating, for example, stroke or skull-brain trauma can be shown in the following animal models.
2. Permanent Focal Cerebral Ischemia Animal model: permanent focal cerebral ischemia ("middle cerebral artery occlusion"=MCA-O). MCA occlusion in rodents is a widely accepted animal model of stroke. Literature: Bederson et al., *Stroke,* 1986, 17, 472–476.

To cause permanent focal cerebral ischemia, the left middle cerebral artery in rats is occluded by electrocoagulation. The resulting infarct volume in cortical (subcortical) regions supplied by the middle cerebral artery is used as a measure for the extent of the stroke-induced neuronal damage.

Substance application: after the occlusion as a continuous i.v infusion (4 hours) of the test substance, started directly after the operation. For evaluation, the animals are sacrificed 7 days after the operation.

In the present invention also includes pharmaceutical preparations which, in addition to inert non-toxic pharmaceutically suitable auxiliaries and carriers, comprise one or more compounds of the general formula (I), or which consist of one or more active compounds of the formula (I), and processes for preparing these preparations.

In these preparations, the active compounds of the formula (I) should be present in a concentration of from 0.1 to 99.5% by weight, preferably from 0.5 to 95% by weight, of the total mixture.

In addition to the active compounds of the formula (I), the pharmaceutical preparations may also comprise other pharmaceutically active compounds.

The pharmaceutical preparations mentioned above can be prepared in a customary manner by known methods using, for example, the auxiliary/auxiliaries or carrier/carriers.

In general, it has been found to be advantageous to administer the active compound(s) of the formula (I) in total amounts of about 0.01 to about 100 mg/kg, preferably in total amounts of about 1 mg/kg to 50 mg/kg, of body weight per 24 hours, if appropriate in the form of a plurality of individual administrations, to obtain the desired result.

However, it may be advantageous, if appropriate, to deviate from the amounts mentioned, depending on the nature and the body weight of the patient treated, on the individual response to the medicament, on the nature and severity of the disorder, on the nature of the preparation and the application, and on the time or interval at which administration takes place.

WORKING EXAMPLES

Example 1

(R)-(−)-2-(4-{[(7-Hydroxy-6-methoxy-3,4-dihydro-2H-chromen-2-yl)methyl]-amino}butyl)-1,2-benzisothiazol-3(2H)-one 1,1-dioxide hydrochloride

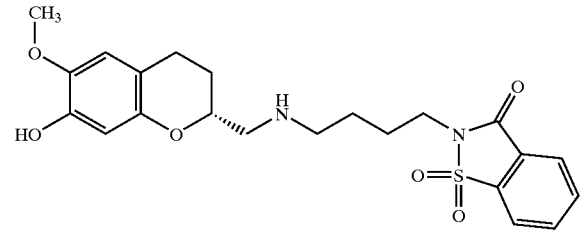

Step a):

Ethyl 7-(benzyloxy)-6-methoxy-4-oxo-4H-chromen-2-carboxylate

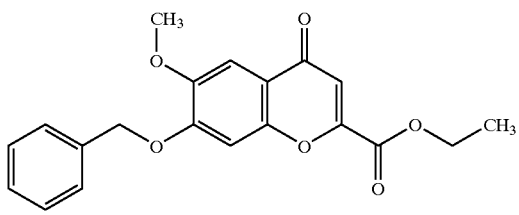

A mixture of 0.37 mmol of 1-[2-hydroxy-5-methoxy-4-(phenylmethoxy)-phenyl]ethanone [Beutler et al., J. Med. Chem. 41, 2333 (1998)] and 1.38 mmol of diethyl oxalate in 2 ml of ethanol is, at room temperature, added over a period of 5 minutes to 1.1 ml of a sodium ethoxide solution prepared from 0.5 g of sodium in 30 ml of ethanol. After 3 hours of heating at reflux, 0.55 ml of concentrated hydrochloric acid is added, and heating at reflux is continued for a further 3 hours. The mixture is diluted with ethanol and the solid is then separated off and discarded. The filtrate is concentrated under reduced pressure, taken up in ethyl acetate and washed with water and then with saturated sodium chloride solution. The mixture is dried over magnesium sulfate and then concentrated, and the residue is purified by flash chromatography (silica gel, mobile phase cyclohexane/ethyl acetate, gradient 10:1 to 1:1). This gives ethyl 7-(benzyloxy)-6-methoxy-4-oxo-4H-chromen-2-carboxylate in a yield of 58% as a colorless solid.

Mp. 168° C.

Step b):

Ethyl 7-hydroxy-6-methoxy-2-chromancarboxylate

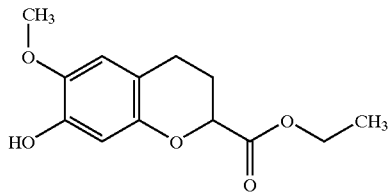

A solution of 7.5 mmol of ethyl 7-(benzyloxy)-6-methoxy-4-oxo-4H-chromen-2-carboxylate in 60 ml of ethyl acetate and 30 ml of glacial acetic acid is hydrogenated in the presence of 1.2 g of 10% palladium on carbon at 3 bar and 50° C. After 4 days, the hydrogenation is terminated and the mixture is diluted with ethyl acetate. The mixture is filtered through kieselguhr and the filtrate is concentrated under reduced pressure. The residue is taken up in ethyl acetate and the organic phase is washed with water and saturated sodium chloride solution. The mixture is dried over sodium sulfate and concentrated, giving ethyl 7-hydroxy-6-methoxy-2-chromancarboxylate in a yield of 94% as a colorless oil which is directly reacted further.

Step c):

Ethyl 7-(benzyloxy)-6-methoxy-2-chromancarboxylate

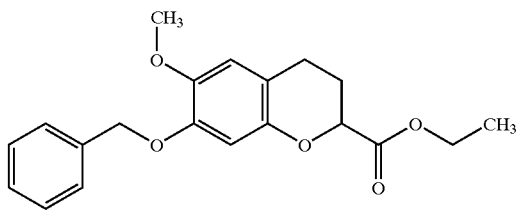

Under argon, 8.9 mmol of a 60% strength suspension of sodium hydride in paraffin oil are added a little at a time to 1.86 g of ethyl 7-hydroxy-6-methoxy-2-chromancarboxylate in 23 ml of dimethylformamide. The mixture is stirred at room temperature for 60 minutes, and 8.1 mmol of benzyl bromide are then added. The reaction mixture is stirred at room temperature for 5 hours. For aqueous work-up (three times washing with water, once with saturated sodium chloride solution), the mixture is diluted with ethyl acetate. The organic phase is dried over sodium sulfate and concentrated. Two recrystallizations from cyclohexane give pure ethyl 7-(benzyloxy)-6-methoxy-2-chromancarboxylate; further product fractions are obtained from the mother liquors of the recrystallizations by preparative HPLC purification (column; chromsil, mobile phase: acetonitrile/water).

Total yield: 72% of theory.

Mp. 100° C.

Step d):

(+)- and (−)-Ethyl 7-(benzyloxy)-6-methoxy-2-chromancarboxylate

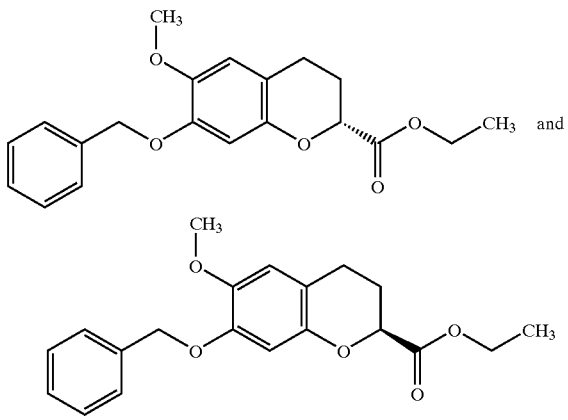

Preparative HPLC separation of the racemic ethyl 7-(benzyloxy)-6-methoxy-2-chromancarboxylate on a chiral phase (Chiracel OD 500×20 mm; isohexane/isopropanol 6:4) gives the (S)-(−)-enantiomer [mp. 95° C., $\alpha_D^{20}$=−12.2° (c=0.6, dichloromethane)] and the (R)-(+)-enantiomer [mp. 94° C., $\alpha_D^{20}$=+11.5° (c=0.5, dichloromethane)] as colorless solids.

Step e):

(R)-(−)-[7-(Benzyloxy)-6-methoxy-3,4-dihydro-2H-chromen-2-yl]methanol

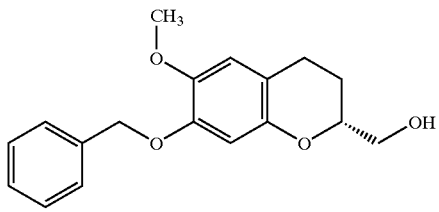

2.6 mmol of (R)-(+)-ethyl 7-(benzyloxy)-6-methoxy-2-chromancarboxylate are dissolved in 9 ml of toluene and, under argon and at room temperature, added dropwise to a solution of 6.5 mmol of sodium bis(2-methoxyethoxy) aluminum dihydride in 18 ml of toluene. After 2 hours at room temperature, the mixture is diluted with ethyl acetate. The mixture is washed twice with water, undissolved particles are filtered off and the filtrate is then washed again with water and then with saturated sodium chloride solution. Drying over sodium sulfate and evaporation under reduced pressure gives a solidifying oil which is purified by flash chromatography (silica gel, mobile phase cyclohexane/ethyl acetate 2:1). This gives, in a yield of 89%, (R)-(−)-[7-(benzyloxy)-6-methoxy-3,4-dihydro-2H-chromen-2-yl] methanol.

Mp. 109–112° C.

$\alpha_D^{20}$=−71° (c=0.5, dichloromethane)

optical purity >99.5% (HPLC on a chiral OD-H column).

Step f):

(R)-[7-(Benzyloxy)-6-methoxy-3,4-dihydro-2H-chromen-2-yl]methylmethane-sulfonate

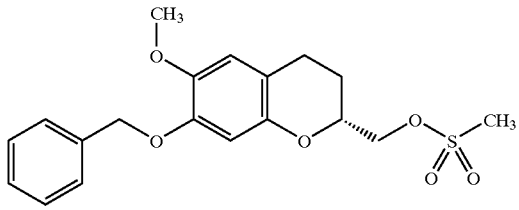

245 mg of methanesulfonyl chloride are added dropwise to a solution of 1.8 mmol of (R)-(−)-[7-(benzyloxy)-6-methoxy-3,4-dihydro-2H-chromen-2-yl]methanol in 0.35 ml of pyridine and 5 ml of dichloromethane. The mixture is stirred overnight and then diluted with dichloromethane. Aqueous work-up (washing with water and sodium chloride solution), drying and concentration gives a crude product which is purified by flash chromatography (silica gel, mobile phase toluene/ethyl acetate, gradient 10:1 to 1:1). The product fraction obtained after evaporation is recrystallized from dichloromethane/cyclohexane. This gives, in a yield of 93%, (R)-[7-(benzyloxy)-6-methoxy-3,4-dihydro-2H-chromen-2-yl]methylmethanesulfonate.

Mp. 147° C.

Step g):

(R)-(−)-[N-Benzyl-N-{[7-(benzyloxy)-6-methoxy-3,4-dihydro-2H-chromen-2-yl]-methyl}amine

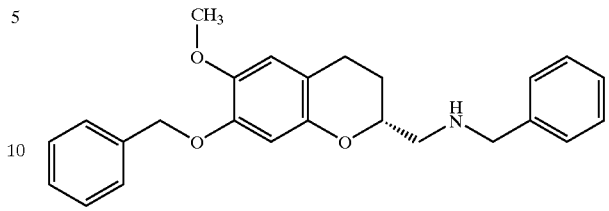

A mixture of 1.4 mmol of (R)-[7-(benzyloxy)-6-methoxy-3,4-dihydro-2H-chromen-2-yl]methylmethanesulfonate, 15 mg of sodium iodide and 1.6 ml of benzylamine is allowed to stand at room temperature for 14 days. The mixture is then heated at 100° C. for 5 hours. After cooling, the reaction mixture is diluted with toluene, and the precipitated solid is filtered off. The filtrate is freed of volatile components, finally at 100° C. and under a reduced pressure of about 1 mbar. The solution of the residue and the ethyl acetate is subjected to aqueous work-up (washing with water and sodium chloride) and dried. The residue obtained after concentration is purified by flash chromatography (silica gel, mobile phase toluene/ethyl acetate, gradient 2:1 to 1:1). The evaporated product fractions are treated with cyclohexane, giving a solid which is recrystallized from cyclohexane. Washing with pentane gives, in a yield of 83%, (R)-(−)-[N-benzyl-N-{[7-(benzyloxy)-6-methoxy-3,4-dihydro-2H-chromen-2-yl]-methyl}amine as colorless crystals.

Mp. 94° C.

$\alpha_D^{20}$=−76.5° (c=0.5, methanol).

Step h):

(R)-(−)-[2-[4-(Benzyl{[7-(benzyloxy)-6-methoxy-3,4-dihydro-2H-chromen-2-yl]-methyl}amino)-2-butynyl]-1,2-benzisothiazol-3(2H)-one 1,1-dioxide

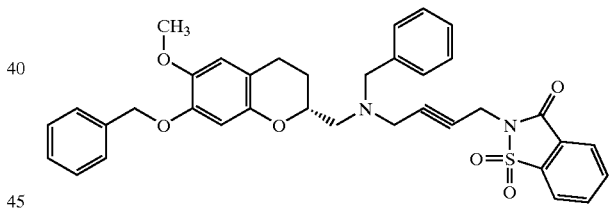

At room temperature and under argon, 42 mg of paraformaldehye, 14 mg of copper(II) acetate and 308 mg of 2-(2-propynyl)-1,2-benzisothiazol-3(2H)-one 1,1-dioxide (obtained from the sodium salt of saccharine and propargyl bromide) are added successively to a solution of 1.1 mmol of (R)-(−)-[N-benzyl-N-{[7-(benzyloxy)-6-methoxy-3,4-dihydro-2H-chromen-2-yl]methyl}amine in 3 ml of dioxane, and the mixture is then heated at 80° C. for 90 minutes. After dilution with ethyl acetate, the mixture is subjected to aqueous work-up (washing with water and saturated sodium chloride solution). The organic phase is dried over sodium sulfate and concentrated. Flash chromatography (silica gel, mobile phase cyclohexane/ethyl acetate 1:1) gives a crude product which is rechromatographed (silica gel, mobile phase dichloromethane, then cyclohexane/ethyl acetate 1:2). In this manner, (R)-(−)-[2-[4-(benzyl {[7-(benzyloxy)-6-methoxy-3,4-dihydro-2H-chromen-2-yl]methyl}-amino)-2-butynyl]-1,2-benzisothiazol-3(2H)-one 1,1-dioxide is obtained as an oil in a yield of 90%.

$\alpha_D^{20}$=−35.2° (c=0.5, methanol).

Step i):

(R)-(−)-2-(4-{[(7-Hydroxy-6-methoxy-3,4-dihydro-2H-chromen-2-yl)methyl]-amino}butyl)-1,2-benzisothiazol-3(2H)-one 1,1-dioxide hydrochloride

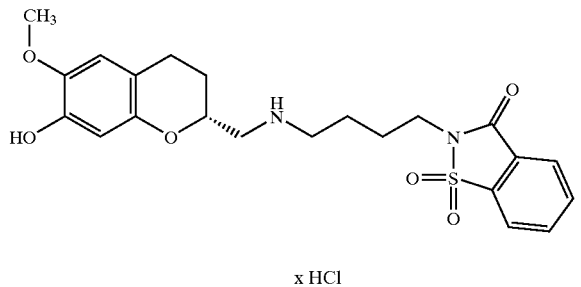

A mixture of 0.88 mmol of (R)-(−)-2-[4-(benzyl{[7-(benzyloxy)-6-methoxy-3,4-dihydro-2H-chromen-2-yl]methyl}amino)-2-butynyl]-1,2-benzisothiazol-3(2H)-one 1,1-dioxide and 0.1 g of 10% palladium on carbon in 7 ml of methanol and 2 ml of concentrated hydrochloric acid is, without external cooling, hydrogenated under atomospheric pressure. After 2 hours, the same amount of catalyst is added, and the hydrogenation is continued for a further 4 hours. The reaction mixture is diluted with dichloromethane and filtered through kieselguhr. The filtrate is washed with saturated sodium chloride solution and dried over sodium sulfate. The oil obtained after evaporation is taken up in a little hot dichloromethane, and cyclohexane is added. Distillative removal of the dichloromethane under reduced pressure results in the formation of crystals. The resulting precipitate is filtered off, washed with cyclohexane and dried under reduced pressure. This gives, in a yield of 64%, (R)-(−)-[2-(4-{[(7-hydroxy-6-methoxy-3,4-dihydro-2H-chromen-2-yl)methyl]-amino}butyl)-1,2-benzisothiazol-3(2H)-one 1,1-dioxide hydrochloride.

Mp. 195–198° C. (with decomposition)

$\alpha_D^{20}$=−65.7° (c=0.5, methanol)

MS (ESI pos): m/z=447 [M+H]$^+$ $^1$H-NMR (200 MHz, DMSO-d$_6$): δ=1.5–2.2 (m, 6H), 2.6–3.2 (m, 6H), 3.65 (s, 3H), 3.75 (m, 2H), 4.2 (m, 1H), 6.25 (s, 1H), 6.6 (s, 1H), 7.9–8.15 (m, 3H), 8.3 (m, 1H), 8.6–9.0 (broad, 2H).

Example 2

2-[4-({[(2R)-6-Hydroxy-3,4-dihydro-2H-chromen-2-yl]methyl}amino)butyl]-1,2-benzisothiazol-3(2H)-one 1,1-dioxide hydrochloride

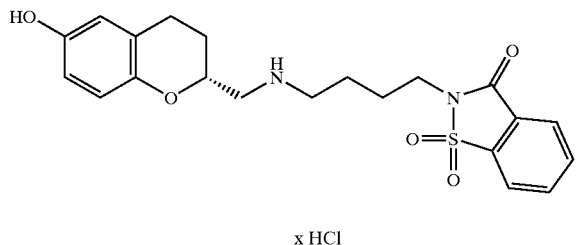

Step a):

Benzyl (2R)-3,4-dihydro-2H-chromen-2-ylmethyl[4-(1,1-dioxido-3-oxo-1,2-benziso-thiazol-2(3H)-yl)butyl]carbamate

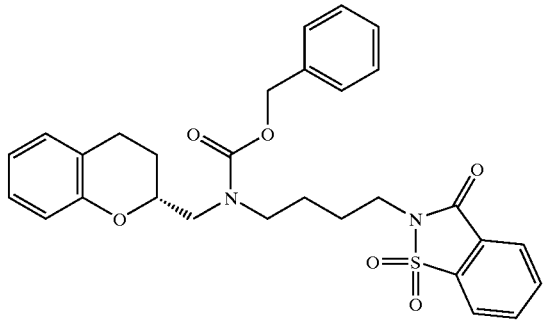

40 ml of water and 2.5 g (30 mmol) of sodium bicarbonate are added to a suspension of 1.2 g (5 mmol) of (−)-(R)-2-[4-[[(3,4-dihydro-2H-1-chromen-2-yl)methyl]-amino]butyl]-1,2-benzisothiazol-3(2H)-one 1,1-dioxide hydrochloride (EP 352 613 B1) in 40 ml of diethyl ether. The mixture is cooled to 0° C. At an internal temperature of at most 5° C., a solution of 1.0 g (6 mmol) of benzyloxycarbonyl chloride in 5 ml of diethyl ether is added dropwise. After 2 hours of stirring at room temperature, the organic phase is separated off and the aqueous phase is extracted with diethyl ether. The combined organic phases are dried over magnesium sulfate and concentrated. Chromatography (silica gel, mobile phase toluene/ethyl acetate, gradient 1:0 to 5:1) gives 2.6 g (90% of theory) of benzyl (2R)-3,4-dihydro-2H-chromen-2-ylmethyl[4-(1,1-dioxido-3-oxo-1,2-benzisothiazol-2(3H)-yl)butyl]carbamate as an oil which is directly reacted without further purification.

R$_f$ (silica gel, toluene/ethyl acetate 3:1)=0.70

Step b):

Benzyl [(2R)-6-acetyl-3,4-dihydro-2H-chromen-2-yl]methyl[4-(1,1-dioxido-3-oxo-1,2-benzisothiazol-2(3H)-yl)butyl]carbamate

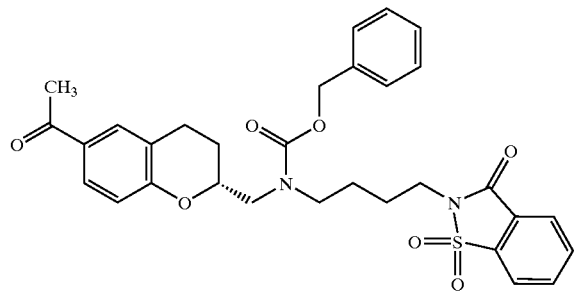

12.7 g (95 mmol) of anhydrous aluminum chloride are suspended in 10 ml of 1,2-dichloroethane. At 0° C., initially 5.9 ml (82 mmol) of acetyl chloride are added. At 0° C., a solution of 34 g (63 mmol) of benzyl (2R)-3,4-dihydro-2H-chromen-2-ylmethyl[4-(1,1-dioxido-3-oxo-1,2-benzisothiazol-2(3H)-yl)butyl]carbamate in 100 ml of 1,2-dichloroethane is slowly added dropwise to this mixture. The reaction is stirred at room temperature overnight. The mixture is poured into ice-water and the organic phase is then separated off and the aqueous phase is repeatedly extracted with dichloromethane. The combined organic extracts are dried over magnesium sulfate and concentrated. The resulting crude product is purified by chromatography (silica gel, mobile phase toluene/ethyl acetate 3:1). This gives 9.6 g (26.5% of theory) of benzyl [(2R)-6-acetyl-3,4-dihydro-2H-chromen-2-yl]methyl[4-(1,1-dioxido-3-oxo-1,2-benzisothiazol-2(3H)-yl)butyl]carbamate.

$R_f$ (silica gel, toluene/ethyl actetate 3:1)=0.32

Step c):

(2R)-2-({[(Benzyloxy)carbonyl][4-(1,1-dioxido-3-oxo-1,2-benzisothiazol-2(3H)-yl)-butyl]amino}methyl)-3,4-dihydro-2H-chromen-6-yl acetate

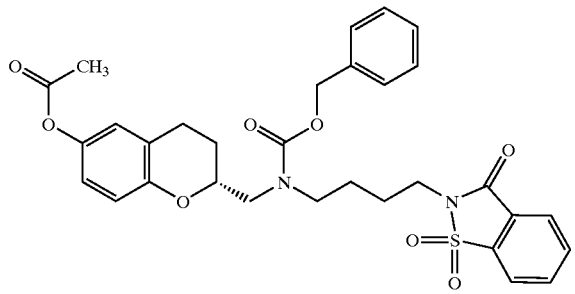

At 0° C. and with exclusion of light, 2.2 g (13 mmol) of m-chloroperoxybenzoic acid are added to 2.9 g (5 mmol) of benzyl [(2R)-6-acetyl-3,4-dihydro-2H-chromen-2-yl]methyl[4-(1,1-dioxido-3-oxo-1,2-benzisothiazol-2(3H)-yl)butyl]carbamate in 30 ml of dichloromethane. At this temperature, 570 mg (5 mmol) of tirfluoroacetic acid are then slowly added dropwise. The mixture is stirred at room temperature overnight and then diluted with dichloromethane, and saturated sodium bicarbonate solution is added. The organic phase is separate off, dried over magnesium sulfate and concentrated. Chromatography (silica gel, mobile phase toluene/ethyl acetate, gradient 1:0 to 3:1) gives 2.8 g (94% of theory) of(2R)-2-({[(benzyloxy)carbonyl][4-(1,1-dioxido-3-oxo-1,2-benzisothiazol-2(3H)-yl)butyl]-amino } methyl)-3,4-dihydro-2H-chromen-6-yl acetate as an oil.

$R_f$ (silica gel, toluene/ethyl acetate 3:1)=0.44

Step d):

2-[4-({[(2R)-6-Hydroxy-3,4-dihydro-2H-chromen-2-yl]methyl}amino)butyl]-1,2-benzisothiazol-3(2H)-one 1,1-dioxide hydrochloride

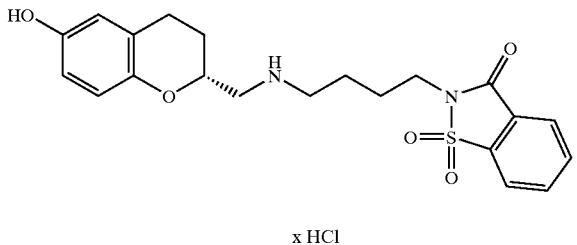

x HCl 2 g of 10% palladium on carbon are added to 11.2 g (19 mmol) of (2R)-2-({[(benzyloxy)carbonyl][4-(1,1-dioxido-3-oxo-1,2-benzisothiazol-2(3H)-yl)-butyl]amino}methyl)-3,4-dihydro-2H-chromen-6-yl acetate in 200 ml of glacial acetic acid and 67 ml of concentrated hydrochloric acid, and the mixture is hydrogenated at 3 bar and room temperature for 4 hours. The catalyst is filtered off, and 5 ml of 25% strength aqueous ammonia are then added and the mixture is concentrated. The residue is purified by chromatography (silica gel, mobile phase dichloromethane/ethanol, gradient 1:0 to 5:1). The resulting product fractions are freed from the solvent by concentration and taken up in ethanol, and 10 ml of a 4 N solution of HCl gas in ethanol are added carefully. After cooling in ice, the resulting solid is filtered off with suction, dissolved in 550 ml of hot ethanol and treated with activated carbon. After filtration, the mixture is concentrated to about 100 ml. The precipitated crystals are filtered off with suction and dried under reduced pressure. This give 3.15 g (37% of theory) of 2-[4-({[(2R)-6-hydroxy-3,4-dihydro-2H-chromen-2-yl]methyl}amino)butyl]-1,2-benzisothiazol-3(2H)-one 1,1-dioxide hydrochloride as colorless crystals.

Mp. 220 to 222° C.

MS (FAB): m/z=417 [M+H]$^+$ $^1$H-NMR (300 MHz, DMSO-$d_6$): δ=1.5–2.1 (m, 6H), 2.6–3.2 (m, 6H), 3.75 (m, 2H), 4.2 (m, 1H), 6.45–6.65 (m, 3H), 7.9–8.15 (m, 3H), 8.3 (m, 1H), 8.6–9.0 (broad, 2H)

| Elemental analysis: | $C_{21}H_{25}ClN_2O_5S$ |
|---|---|
| | C: calc. 55.7, found 56.0; H: calc.. 5.6, found 5.7 |
| | N: calc. 6.2, found 6.2; S: calc. 7.1, found 7.1 |

Example 3

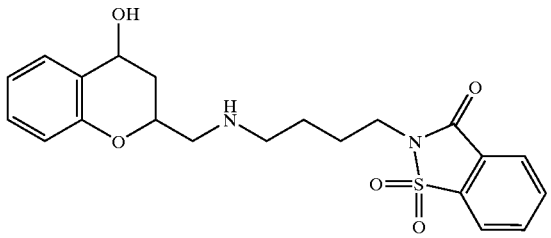

Step a):

4-Hydroxychroman-2-carboxylic acid

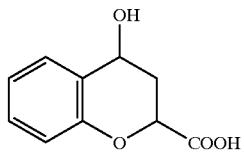

1 g (5.2 mmol) of chromone-2-carboxylic acid is dissolved in 25 ml of 1,4-dioxane and 5 ml of dry ethanol. 1 g (26.3 mmol) of sodium borohydride is added, and the mixture is then heated at reflux for 1 hour. The mixture is cooled to room temperature and solidified with 1 ml of 1 M hydrochloric acid and then with 4.5 ml of 6 M hydrochloric acid. The organic phase is separated off and the aqueous phase is extracted twice with in each case 20 ml of diethyl ether. The organic phases are combined and evaporated to dryness. The residue is dissolved in a solvent mixture of 1.5% acetic acid and 5% methanol (v/v) in dichloromethane, and the product is isolated chromatographically, under the following conditions: column Lobar® LiChroprep® Si 60, size B, column temperature room temperature, mobile phase 1.5% acetic acid and 5% methanol (v/v) in dichloromethane, flow rate 15 ml/min, UV detection at 230 nm. The product-containing fractions are combined and evaporated to dryness.

Yield: 420 mg (37% of theory)

GC/MS (after methylation): m/z=208 [M]$^+$ (methyl ester)

GC/MS (after silylation): m/z=338 [M]$^+$ (bistrimethylsilyl derivative)

$^1$H-NMR (400 MHz, CD$_3$OD, adjusted to δ=3.30 with CD$_2$HOD): δ=2.16 (H-3a, 1H, ddd); 2.48 (H-3e, 1H, ddd);

4.79 (H-2a, 1H, dd); 4.88 (H-4a, 1H, dd); 6.86 (H-8, 1H, d); 6.92 (H-6, 1H, dt); 7.16 (H-7, 1H, dt); 7.37 (H-5, 1H, d).
Step b):

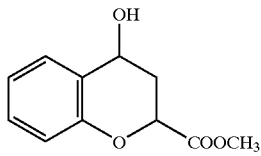

250 mg of 4-hydroxychroman-2-carboxylic acid are suspended in 4.5 ml of diethyl ether, a solution of about 4.5 mmol of diazomethane in 4.5 ml of diethyl ether is added and the mixture is stirred at room temperature for 30 minutes. The mixture is evaporated to dryness, giving the product as an oily residue.

Yield: 268 mg (quant.)

$^1$H-NMR (400 MHz, $CD_3OD$, adjusted to δ=3.30 with $CD_2HOD$): δ=2.26 (H-3a, 1H, ddd); 2.66 (H-3e, 1H, ddd); 3.67 ($CH_3O$, 3H, s); 4.79 (H-2a, 1H, dd); 4.92 (H-4a, 1H, dd); 6.9 (H-8/H-6, 2H, m); 7.2 (H-7/H-5, 2H, m).
Step c):
N-Benzyl-4-(tert-butyldimethylsilanyloxy)chroman-2-carboxamide

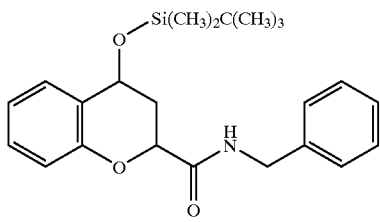

Method 1

55 mg (0.24 mmol) of methyl 4-hydroxychroman-2-carboxylate are dissolved in 0.25 ml of ethylene glycol dimethyl ether. 0.15 ml (1.37 mmol) of benzylamine and 5 mg (0.04 mmol) of lithium iodide are added, and the mixture is then stirred at 60° C. for 3 hours. The product is precipitated using 1 ml of 0.1 M hydrochloric acid and the solid is filtered off, washed with water and dried in a desiccator over blue gel.

80 mg (0.28 mmol) of the N-benzyl-4-hydroxychroman-2-carboxylamine obtained in this manner are dissolved in 2 ml of dichloromethane, and 150 μl (1.29 mmol) of 2,6-lutidine are added. 150 μl (0.65 mmol) of tert-butyldimethylsilyl trifluoromethanesulfonate are then added, and the solution is stirred at room temperature for 8 hours. The reaction is terminated by addition of 0.53 ml of 10% strength ammonium chloride solution, and another 0.5 ml of dichloromethane is then added. The product-containing organic phase is washed 7 times with in each case 0.73 ml of 0.1 M hydrochloric acid and then with 0.29 ml of a saturated sodium bicarbonate solution and then evaporated to dryness. The crude product is purified by HPLC (see below).
Method 2

268 mg (1.2 mmol) of methyl 4-hydroxychroman-2-carboxylate are dissolved in 2.5 ml of dichloromethane. 0.6 ml (5.15 mmol) of 2,6-lutidine and 0.6 ml (2.61 mmol) of tert-butyldimethylsilyl trifluoromethanesulfonate are added, and the solution is then stirred at room temperature for 6 hours. The reaction is terminated by addition of 2 ml of a 10% strength ammonium chloride solution and the product-containing organic phase is then washed 7 times with in each case 3 ml of 0.1 M hydrochloric acid and then with 1 ml of a saturated sodium bicarbonate solution and then evaporated to dryness.

430 mg (1.33 mmol) of the methyl 4-(tert-butyldimethylsilanyloxy)chroman-2-carboxylate obtained in this manner are dissolved in 1.25 ml of ethylene glycol dimethyl ether, and 0.765 ml (7 mmol) of benzylamine are added. 25.5 mg (0.19 mmol) of lithium iodide are added, and the reaction mixture is then stirred at 70° C. for 3 hours. The product is precipitated by addition of 5 ml of 0.1 M hydrochloric acid. The supernatant is decanted and the residue is washed with 2 ml of water. The residue is then dissolved in 1 ml of dichloromethane, and the product-containing organic phase is evaporated to dryness.

The crude products obtained by Method 1 and Method 2 are combined and purified by preparative HPLC chromatography under the following conditions: column Nucleosil® 100 C-18, 125×16 mm (particle size 7 μm), column temperature room temperature, mobile phase 75% acetonitrile/25% water (v/v), flow rate 6 ml/min, UV detection at 230 nm. The product-containing fractions are combined and evaporated to dryness.

Yield: 265 mg (46% of theory)

$^1$H-NMR (400 MHz, $CD_3OD$, adjusted to δ=3.30 with $CD_2HOD$): δ=0.20/0.23 (dimethylsilyl, 3H, s/3H, s); 0.96 (t-butyl, 9H, s); 1.97 (H-3a, 1H, m); 2.54 (H-3e, 1H, ddd); 4.41/4.50 ($CH_2$-phenyl, 2H, AB); 4.72 (H-2a, 1H, dd); 5.09 (H-4a, 1H, dd); 6.91 (H-8, 1H, d); 6.94 (H-6, 1H, t); 7.15 (H-7, 1H, t); 7.20–7.35 (H-5 and phenyl, 6H, m).
Step d):
Benzyl-[4-(tert-butyldimethylsilanyloxy)-chroman-2-ylmethyl]amine

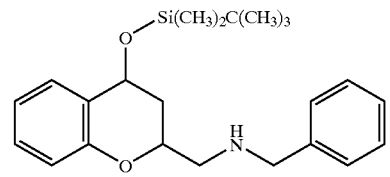

A solution of 265 mg (0.66 mmol) of N-benzyl-4-(tert-butyldimethylsilanyloxy)-chroman-2-carboxamide in 2 ml of toluene is cooled in an ice bath, and 2 ml of sodium bis-(2-methoxyethoxy)aluminum dihydride (70% strength solution in toluene) are added. The reaction mixture is stirred at 60° C. for 2 hours and at room temperature overnight. 10 ml of 1 M aqueous sodium hydroxide solution are then added a little at a time, and the mixture is extracted with 20 ml of dichloromethane and again with 10 ml of dichloromethane. The combined organic phases are washed with 10 ml of water and evaporated to dryness. The product is obtained as an oily residue.

Yield: 226 mg (89% of theory)

$^1$H-NMR (400 MHz, $CD_3OD$, adjusted to δ=3.30 with $CD_2HOD$): δ=0.17/0.21 (dimethylsilyl, 3H, s/3H, s); 0.96 (t-butyl, 9H, s); 1.75 (H-3a, 1H, m); 2.18 (H-3e, 1H, ddd); 2.77 (H-9, 1H, dd); 2.90 (H-9', 1H, dd); 3.84 ($CH_2$-phenyl, 2H, s); 4.30 (H-2a, 1H, m); 5.01 (H-4a, 1H, dd); 6.76 (H-8, 1H, d); 6.86 (H-6, 1H, t); 7.10 (H-7, 1H, t); 7.20–7.45 (H-5 and phenyl, 6H, m).

Step e):
2-(4-{Benzyl-[4-(tert-butyldimethylsilanyloxy)chroman-2-ylmethyl]amino}butyl)-1,1-dioxo-1,2-dihydro-1λ⁶-benzo[d]isothiazol-3-one

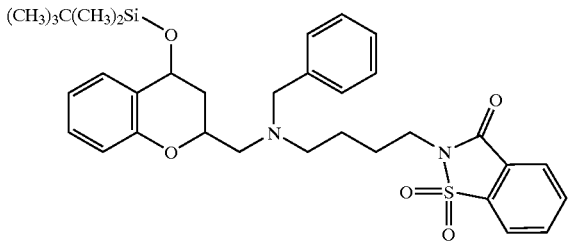

380 mg (1.19 mmol) of 2-(4-bromobutyl)-1,1-dioxo-1,2-dihydro-1λ⁶-benzo[d]isothiazol-3-one and 263 μl (1.51 mmol) of N-ethyldiisopropylamine are added to a solution of 224 mg (0.58 mmol) of benzyl-[4-(tert-butyldimethylsilanyloxy)chroman-2-ylmethyl]amine in 1.25 ml of dry N-methylpyrrolidinone. The reaction mixture is stirred at 120° C. for 3 hours. After cooling to room temperature, 2 ml of water are added, resulting in the precipitation of a dark, viscous product. The supernatant is decanted and the residue is washed twice with in each case 1.5 ml of water. The product is then dissolved in 3 ml of dichloromethane, the residue water is removed by drying and the solution is evaporated to dryness. The crude product is purified by HPLC chromatography under the following conditions: column Nucleosil® 100 C-18, 125×16 mm (particle size 7 μm), column temperature room temperature, mobile phase 85% acetonitrile/15% water (v/v), flow rate 6 ml/min, UV detection at 230 nm. The product-containing fractions are combined and evaporated to dryness. The residue is dissolved in 2.5 ml of ethanol and 6 ml of acetone and again evaporated to dryness. The product is dried in a desiccator over blue gel.

Yield: 121 mg (33% of theory)
MS (EI): m/z=621 [M+H]⁺
¹H-NMR (400 MHz, CD₃OD, adjusted to δ=3.30 with CD₂HOD): δ=0.11/0.16 (dimethylsilyl, 3H, s/3H, s); 0.92 (t-butyl, 9H, s); 1.51 (H-3a, 1H, m); 1.63 (H-11, 2H, m); 1.88 (H-12, 2H, m); 2.26 (H-3e, 1H, ddd); 2.6 (H-9 and H-10/H-10', 3H, m); 2.76 (H-9', 1H, dd); 3.58/3.73 (CH₂-phenyl, 2H, AB); 3.74 (H-13, 2H, t); 4.17 (H-2a, 1H, m); 4.91 (H-4a, 1H, dd); 6.67 (H-8, 1H, d); 6.82 (H-6, 1H, t); 7.04 (H-7, 1H, t); 7.15–7.40 (H-5 and phenyl, 6H, m); 7.90 (H-16, 1H, dt); 7.95 (H-15, 1H, dt); 8.03 (H-14/H-17, 2H, d).

Step f):
2-(4-{[4-tert-Butyldimethylsilanyloxy)chroman-2-ylmethyl]amino}butyl)-1,1-dioxo-1,2-dihydro-1λ⁶-benzo[d]isothiazol-3-one

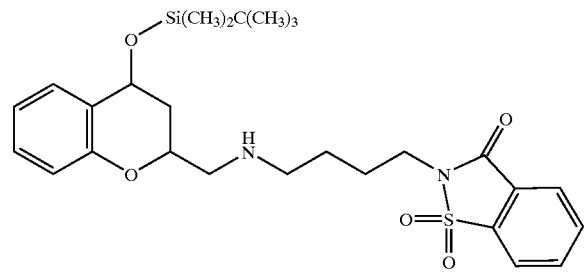

120 mg (0.19 mmol) of 2-(4-{benzyl-[4-(tert-butyldimethylsilanyloxy)chroman-2-ylmethyl]amino}butyl)-1,1-dioxo-1,2-dihydro-1λ⁶-benizo[d]isothiazol-3-one are dissolved in 2 ml of methanol and 1 ml of acetic acid, and 100 mg of Pearlman catalyst (20% Pd(OH)₂ an activated carbon) are added. At room temperature, hydrogen is introduced for 4 hours. After filtration, the mother liquor is concentrated to dryness. The crude product is reacted directly, without further purification.

Yield: 107 mg
MS (EI): m/z=531 [M+H]⁺

Step g):
2-{4-[(4-Hydroxychroman-2-ylmethyl)amino]butyl}-1,1-dioxo-1,2-dihydro-1λ⁶-benzo[d]isothiazol-3-one

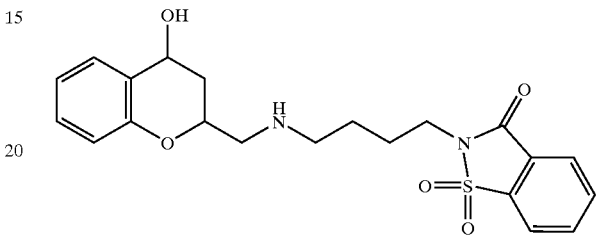

81 mg of 2-(4-{[4-tert-butyldimethylsilanyloxy)chroman-2-ylmethyl]amino}butyl)-1,1-dioxo-1,2-dihydro-1λ⁶-benzo[d]isothiazol-3-one are dissolved in 4 ml of 1 M hydrochloric acid and 4 ml of methanol. The solution is stirred at room temperature overnight. Using sodium bicarbonate, the pH is adjusted to 8, and the mixture is then extracted three times with in each case 3 ml of dichloromethane. The combined organic phases are combined with a solution of 16 mg of product from a preliminary experiment, dried over sodium sulfate and evaporated to dryness.

Yield: 74 mg
¹H-NMR (500 MHz, CD₃OD, adjusted to δ=3.30 with CD₂HOD): δ=1.68 (H-11, 2H, m); 1.74 (H-3a, 1H, ddd); 1.89 (H-12, 2H, m); 2.24 (H-3e, 1H, ddd); 2.85 (H-9, 1H, dd); 2.75 (H-10/H-10', 3H, t); 2.93 (H-9', 1H, dd); 3.81 (H-13, 2H, t); 4.29 (H-2a, 1H, m); 4.87* (H-4a, 1H, dd); 6.77 (H-8, 1H, d); 6.88 (H-6, 1H, t); 7.10 (H-7, 1H, t); 7.41 (H-5, 1H, dd); 7.93 (H-16, 1H, dt); 7.98 (H-15, 1H, dt); 8.05 (H-14, 1H, m); 8.07 (H-17, 1H, m). *This value was measured at 50° C.

What is claimed is:
1. A compound of the general formula (I),

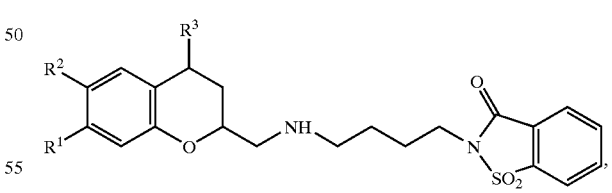

in which
the radicals R¹, R² and R³ are as defined below:

| R¹ | R² | R³ |
|---|---|---|
| OH | H | H; |
| H | OH | H; |
| H | H | OH; |

-continued

| R¹ | R² | R³ |
|---|---|---|
| OH | OH | H; |
| OH | H | OH; |
| H | OH | OH or |
| OH | OH | OH, | or a salt, hydrate or solvate thereof.

2. A compound as claimed in claim 1, where the compound has the R configuration in the 2-position of the chroman ring.

3. A pharmaceutical composition comprising at least one compound as claimed in claim 1 or 2 and customary auxiliaries and additives.

4. A method for preparing a pharmaceutical composition comprising at least one compound as claimed in claim 1 or 2, wherein the active compounds are converted into a suitable administration form using customary auxiliaries and additives.

5. A method for treating stroke or skull-brain trauma comprising administering to a subject in need thereof an effective amount of a compound of claim 1 or 2.

* * * * *